US006596070B1

(12) United States Patent
Schmidt et al.

(10) Patent No.: US 6,596,070 B1
(45) Date of Patent: Jul. 22, 2003

(54) INTERFERENCE PIGMENTS

(75) Inventors: Christoph Schmidt, Kriftel (DE);
Gerhard Pfaff, Münster (DE);
Christina Schank, Mühltal (DE);
Sabine Schoen, Darmstadt (DE)

(73) Assignee: Merck Patent Gesellschaft, Darmstadt (DE)

( * ) Notice: Subject to any disclaimer, the term of this patent is extended or adjusted under 35 U.S.C. 154(b) by 0 days.

(21) Appl. No.: 09/529,619

(22) PCT Filed: Oct. 17, 1998

(86) PCT No.: PCT/EP98/06508

§ 371 (c)(1),
(2), (4) Date: Apr. 17, 2000

(87) PCT Pub. No.: WO99/20695

PCT Pub. Date: Apr. 29, 1999

(30) Foreign Application Priority Data

Oct. 17, 1997 (DE) .......................... 197 46 067

(51) Int. Cl.[7] .......................... C04B 14/20; C09C 1/36; B32B 15/02; B32B 17/02
(52) U.S. Cl. .................. 106/417; 106/415; 106/418; 106/436; 106/438; 106/439; 106/442; 428/404
(58) Field of Search ................... 106/415, 417, 106/418, 436, 438, 439, 442; 428/404

(56) References Cited

U.S. PATENT DOCUMENTS

| | | | |
|---|---|---|---|
| 3,767,443 A | 10/1973 | Clark et al. ................. | 106/291 |
| 4,017,326 A | 4/1977 | Davis ......................... | 106/291 |
| 4,168,986 A | 9/1979 | Venis, Jr. .................... | 106/291 |
| 5,573,584 A * | 11/1996 | Ostertag et al. ............. | 106/417 |
| 5,624,486 A * | 4/1997 | Schmid et al. .............. | 106/404 |
| 5,958,125 A * | 9/1999 | Schmid et al. .............. | 106/417 |
| 6,132,873 A * | 10/2000 | Dietz et al. ................. | 428/404 |
| 6,156,115 A * | 12/2000 | Pfaff et al. .................. | 106/403 |
| 6,238,471 B1 * | 5/2001 | Vogt et al. .................. | 106/417 |
| 6,238,472 B1 * | 5/2001 | Andes et al. ................ | 106/430 |
| 6,267,810 B1 * | 7/2001 | Pfaff et al. .................. | 106/415 |
| 6,280,520 B1 * | 8/2001 | Andes et al. ................ | 106/415 |
| 6,284,032 B2 * | 9/2001 | Andes et al. ................ | 106/436 |
| 6,500,251 B1 * | 12/2002 | Andes et al. ................ | 106/415 |

FOREIGN PATENT DOCUMENTS

| | | | |
|---|---|---|---|
| DE | 2215191 | * | 3/1972 |
| WO | 9401498 | | 1/1994 |
| WO | 9812266 | | 3/1998 |

* cited by examiner

*Primary Examiner*—Mark L. Bell
*Assistant Examiner*—Patricia L. Hailey
(74) *Attorney, Agent, or Firm*—Millen, White, Zelano & Branigan, P.C.

(57) ABSTRACT

The present invention relates to interference pigments on the basis of multiply coated, platelet-shaped substrates which comprise at least one layer sequence comprising (A) a coating having a refractive index $n \geq 2.0$, (B) a colorless coating having a refractive index $n \leq 1.8$, and (C) a nonabsorbing coating of high refractive index, and, if desired, (D) an external protective layer.

13 Claims, No Drawings

INTERFERENCE PIGMENTS

The present invention relates to interference pigments based on multiply coated platelet-shaped substrates.

Lustre pigments or special-effect pigments are employed in numerous fields in industry, especially in the sector of automotive finishes, in decorative coating, in plastics, in paints, in printing inks and in cosmetic formulations.

Lustre pigments which exhibit an angle-dependent colour change between two or more interference colours have a play of colour which makes them of particular interest for automotive finishes and in connection with counterfeit-protected documents of value. Pigments of this kind on the basis of multiply coated platelet-shaped substrates are known.

Interference pigments consist generally of platelet-shaped substrates with a thickness of from 200 to 1000 nm which are coated with highly refractive metal oxides or metal oxide mixtures with a thickness of from 50 to 300 nm. The optical properties of these pigments are critically determined by the refractive index of the metal oxide layer. In addition to the possibility of using chemical vapour deposition (CVD) or physical vapour deposition (PVD) techniques to prepare metal oxide layers having high densities and so refractive indices that lie close to the optimum, the deposition of metal oxides on finely divided, platelet-shaped substrates is frequently accomplished by titrating aqueous, usually acidic metal salt solutions against sodium hydroxide solution in the presence of a substrate, as described, for example, in DE 14 67 468 and DE 20 09 566.

A disadvantage of the vapour deposition technique is the high costs it entails. For instance, U.S. Pat. No. 4,434,010 discloses a multilayer interference pigment consisting of a central layer of a reflective metal, such as aluminium, and alternating layers of two transparent dielectric materials of high and low refractive index respectively, such as titanium dioxide and silicon dioxide, for example. This multilayer pigment is used preferably for counterfeit-protected securities.

JP H7-759 discloses a multilayer interference pigment with metallic lustre, for which a substrate is coated with alternate layers of titanium dioxide and silicon dioxide. The substrate comprises flakes of aluminium, gold or silver, or of mica or glass, with a coating of metals. The depth effect which is characteristic of and desired for interference pigments, however, cannot be generated. This is because of the total reflection of the light at the metal layer which forms the core. Consequently, the interference effect remains limited to the layers which are located on the metal layer. Furthermore, the lack of transparency of the substrate greatly restricts the diverse possibilities for combination with further pigments in applications-related formulations.

U.S. Pat. No. 3,438,796 and U.S. Pat. No. 5,135,812 describe, for example, metal lustre pigments having a central opaque aluminium film coated on both sides in alternation with dielectric films of low refractive index, such as silicon dioxide or magnesium fluoride, and with partially transparent metal films, such as films of chromium or aluminium, for example. Owing to the preparation process, the central metal film of these pigments is coated only on the top and bottom sides of the platelets, while the side areas constitute broken edges and lie open towards the medium.

DE 44 05 494, DE 44 37 753, DE 195 16 181 and DE 195 15 988 disclose lustre pigments prepared by coating metal platelets, especially aluminium flakes, with metal oxide layers of low refractive index, such as with a silicon dioxide layer, and with non-selectively absorbing metal oxide layers or metal layers of high refractive index, using CVD or wet-chemical techniques.

Lustre pigments based on metal substrates frequently have good performance properties, including good opacity, but the result on application, such as in the paint, for example, is a "hard" metallic lustre, which is frequently unwanted.

Lustre pigments based on transparent platelet-shaped substrates which do not have this "hard" metallic lustre are the subject of WO 93/12182. Mica flakes are covered with a metal oxide layer of high refractive index, such as $TiO_2$, and with a non-selectively absorbing layer. Depending on the thickness of the $TiO_2$ layer, when viewed straight on these pigments exhibit a particular interference colour which becomes increasingly weaker as the viewing angle becomes more oblique and which finally flips to grey or black. The interference colour does not change, but a decrease is found in the colour saturation.

JP 1992/93206 claims lustre pigments on the basis of glass flakes or mica particles which are covered with an opaque metal layer and with alternating layers of $SiO_2$ and $TiO_2$.

EP 0 753 545 discloses lustre pigments based on multiply coated, nonmetallic, platelet-shaped substrates which are of high refractive index, are at least partially transparent to visible light and have at least one layer assembly comprising a colourless coating of low refractive index and a reflective coating which absorbs selectively or nonselectively. Disadvantages of this invention are the technically very complex and costly preparation process and the frequent difficulty in reproducing the pigments in the desired product quality.

The object of the present invention is to provide an essentially transparent interference pigment having strong interference colours and/or a strong angular dependence of the interference colours which is notable for its advantageous performance properties and which at the same time can be prepared in a simple manner.

Surprisingly, an interference pigment has now been found which is based on multiply coated, platelet-shaped substrates and comprises a particular arrangement of optically functional layers by means of which particular optical effects are achieved.

The invention therefore provides interference pigments on the basis of multiply coated, platelet-shaped substrates which comprise at least one layer sequence comprising (A) a coating having a refractive index $n \geq 2.0$, (B) a colourless coating having a refractive index $n \leq 1.8$, and (C) a nonabsorbing coating of high refractive index, and, if desired, (D) an external protective layer.

The invention also provides for the use of the pigments of the invention in paints, lacquers, printing inks, plastics, ceramic materials, glasses and cosmetic formulations.

Suitable base substrates for the multilayer pigments of the invention are firstly opaque and secondly transparent platelet-shaped substances. Preferred substrates are phyllosilicates and metal oxide-coated, platelet-shaped materials. Of particular suitability are natural and synthetic micas, talc, kaolin, platelet-shaped iron oxides, bismuth oxychloride, flakes of glass, $SiO_2$, $Al_2O_3$ or $TiO_2$, synthetic ceramic flakes, carrier-free synthetic platelets, LCPs or other comparable materials.

The size of the base substrates per se is not critical and can be matched to the particular target application. In general, the platelet-shaped substrates have a thickness of between 0.1 and 5 $\mu$m, in particular between 0.2 and 4.5 $\mu$m. The extent in the two other dimensions is usually between 1 and 250 μm, preferably between 2 and 200 μm and, in particular, between 5 and 50 μm.

The thickness of the individual layers of high and low refractive index on the base substrate is essential for the optical properties of the pigment. For a pigment with intensive interference colours, the thickness of the individual layers must be adjusted precisely with respect to one another.

If n is the refractive index of a thin layer and d its thickness, the interference colour of this layer is defined by the product n·d (n·d=optical thickness). The colours which result from such a film under perpendicular light incidence in reflected light result from an intensification of the light of wavelength $$\lambda = \frac{4}{2N-1} \cdot n \cdot d$$

and by an attenuation of the light of wavelength $$\lambda = \frac{2}{N} \cdot n \cdot d$$

where N is a positive integer.

The variation in colour which results with increasing film thickness is a consequence of the intensification or attenuation of certain light wavelengths through interference. If two or more layers in a multilayer pigment possess the same optical thickness, the colour of the reflected light becomes more intense as the number of layers increases. In addition to this, it is possible through an appropriate choice of layer thicknesses to achieve a particularly strong variation of the colour as a function of the viewing angle. A pronounced, so-called colour flop is developed. The thickness of the individual metal oxide layers, irrespective of their refractive index, depends on the field of use and is generally from 10 to 1000 nm, preferably from 15 to 800 nm and, in particular, 20–600 nm.

The lustre pigments of the invention feature a coating (A) of high refractive index in combination with a colourless coating (B) of low refractive index and located thereon a nonabsorbing coating of high refractive index. The pigments can comprise two or more, identical or different combinations of layer assemblies, although preference is given to covering the substrate with only one layer assembly (A)+(B)+(C). In order to make the colour flop more intense the pigment of the invention may comprise up to 4 layer assemblies, although the thickness of all of the layers on the substrate should not exceed 3 μm.

The layer (A) of high refractive index has a refractive index n≧2.0, preferably n≧2.1. Materials suitable as the layer material (A) are all materials known to the skilled worker which are of high refractive index, are filmlike and can be applied permanently to the substrate particles. Particularly suitable materials are metal oxides or metal oxide mixtures, such as $TiO_2$, $Fe_2O_3$, $ZrO_2$, ZnO or $SnO_2$, or compounds of high refractive index such as, for example, iron titanates, iron oxide hydrates, titanium suboxides, chromium oxide, bismuth vanadate, cobalt aluminate, and also mixtures or mixed phases of these compounds with one another or with other metal oxides.

The thickness of the layer (A) is 10–550 nm, preferably 15–400 nm and, in particular, 20–350 nm.

Colourless materials of low refractive index suitable for the coating (B) are preferably metal oxides or the corresponding oxide hydrates, such as $SiO_2$, $Al_2O_3$, AlO(OH), $B_2O_3$ or a mixture of these metal oxides. The thickness of the layer (B) is 10–1000 nm, preferably 20–800 nm and, in particular, 30–600 nm.

Materials particularly suitable for the non-absorbing coating (C) of high refractive index are colourless metal oxides such as $TiO_2$, $ZrO_2$, $SnO_2$, ZnO and BiOCl, and also mixtures thereof. The thickness of the layer (C) is 10–550 nm, preferably 15–400 nm and, in particular, 20–350 nm.

In addition to the standard layer assembly (A)+(B)+(C), which may be present up to four times in the pigment of the invention, there are other preferred embodiments. For instance, between the substrate (S) and the layer (A), between the layer (A) and (B), between layer (B) and (C) and/or between layer (C) and the top layer (D) the pigment of the invention may have a further absorbing or nonabsorbing layer [(S1), (A1), (B1), (C1)]. The thickness of the interlayers is 1–50 nm, preferably 1–40 nm and, in particular, 1–30 nm.

A particularly preferred embodiment is the coating of the substrate with the following layer assembly:
(S1) optional, $SnO_2$
(A) $TiO_2$ or $Fe_2O_3$
(B) $SiO_2$
(B1) optional, $SnO_2$
(C) $TiO_2$
(D) final coating related to application Coating the substrates with layers (A) and (C) of high refractive index, a layer (B) of low refractive index and, if desired, further coloured or colourless coatings produces pigments whose colour, gloss, opacity and angular dependence of perceived colour can be varied within wide limits.

The pigments of the invention are easy to produce by virtue of the generation of two or more interference layers of high and low refractive index, precisely defined thickness and smooth surface on the finely divided, platelet-shaped substrates.

The metal oxide layers are preferably applied by wet-chemical means, it being possible to use the wet-chemical coating techniques developed for the production of pearl lustre pigments; techniques of this kind are described, for example, in DE 14 67 468, DE 19 59 988, DE 20 09 566, DE 22 14 545, DE 22 15 191, DE 22 44 298, DE 23 13 331, DE 25 22 572, DE 31 37 808, DE 31 37 809, DE 31 51 343, DE 31 51 354, DE 31 51 355, DE 32 11 602, DE 32 35 017 or else in further patent documents and other publications.

In the case of wet coating, the substrate particles are suspended in water, and one or more hydrolysable metal salts are added at a pH which is appropriate for hydrolysis and is chosen such that the metal oxides or metal oxide hydrates are precipitated directly onto the platelets without any instances of secondary precipitation. The pH is kept constant usually by simultaneous metered addition of a base and/or acid. Subsequently, the pigments are separated off, washed and dried and, if desired, are calcined, it being possible to optimize the calcination temperature in respect of the particular coating present. In general, the calcination temperatures are between 250 and 1000° C., preferably between 350 and 900° C. If desired, following the application of individual coatings the pigments can be separated off, dried and, if desired, calcined before being resuspended for the application of further layers by precipitation.

Coating can also take place in a fluidized-bed reactor by means of gas-phase coating, in which case it is possible, for example, to make appropriate use of the techniques proposed in EP 0 045 851 and EP 0 106 235 for preparing pearl lustre pigments.

The metal oxide of high refractive index used is preferably titanium dioxide and/or iron oxide, and the metal oxide of low refractive index preferably used is silicon dioxide.

For the application of the titanium dioxide layers, preference is given to the technique described in U.S. Pat. No. 3,553,001.

An aqueous titanium salt solution is added slowly to a suspension, heated to about 50–100° C., of the material to be coated, and a substantially constant pH of about 0.5–5 is maintained by simultaneous metered addition of a base, for example aqueous ammonia solution or aqueous alkali metal hydroxide solution. As soon as the desired layer thickness of the $TiO_2$ precipitate has been reached, the addition of both titanium salt solution and base is terminated.

This technique, also referred to as the titration process, is notable for the fact that it avoids an excess of titanium salt. This is achieved by supplying to the hydrolysis only that quantity per unit time which is necessary for uniform coating with the hydrated $TiO_2$ and which can be received per unit time by the available surface area of the particles to be coated. There is therefore no production of hydrated titanium dioxide particles not precipitated on the surface to be coated.

The application of the silicon dioxide layers can be performed, for example, as follows. A potassium or sodium silicate solution is metered into a suspension, heated to about 50–100° C., of the substrate that is to be coated. The pH is held constant at about 6–9 by simultaneous addition of a dilute mineral acid, such as HCl, $HNO_3$ or $H_2SO_4$. As soon as the desired layer thickness of $SiO_2$ has been reached, the addition of the silicate solution is terminated. The batch is subsequently stirred for about 0.5 h.

In order to enhance the light stability and weather stability it is frequently advisable to subject the finished pigment to an aftercoating or after-treatment process, depending on the field of use. Suitable such processes are those described, for example, in DE-C 22 15 191, DE-A 31 51 354, DE-A 32 35 017 or DE-A 33 34 598. Such aftercoating further increases the chemical stability or facilitates the handling of the pigment, especially its incorporation into different media.

The pigments of the invention are compatible with a large number of colour systems, preferably from the sector of lacquers, paints and printing inks, especially security printing inks. Owing to the uncopyable optical effects, the pigments of the invention can be used in particular for producing counterfeit-protected documents of value, such as bank notes, cheques, cheque cards, credit cards, identity cards, etc. In addition, the pigments are also suitable for the laser marking of paper and plastics and for applications in the agricultural sector, such as for glasshouse films, for example.

The invention therefore also provides for the in use of the pigments in formulations such as paints, printing inks, lacquers, plastics, ceramic materials and glasses and for cosmetics preparations.

It is of course the case that for the various target applications the multilayer pigments can also be employed advantageously in blends with other pigments, examples being transparent and hiding white, coloured and black pigments, and with platelet-shaped iron oxides, organic pigments, holographic pigments, LCPs (liquid crystal polymers) and conventional transparent, coloured and black lustre pigments based on metal oxide-coated mica and $SiO_2$ platelets, etc. The multilayer pigments can be mixed in any proportion with customary commercial pigments and extenders.

The examples which follow are intended to illustrate the invention yet without placing any limitation on it.

EXAMPLES

Example 1

100 g of mica (PSD 10–60 μm) in 2 l of deionized water are heated to 80° C. At this temperature, 430 g of iron(III) chloride solution (14.25% Fe) are metered in with vigorous stirring. In the course of this addition, the pH is held constant at 4.0 using aqueous sodium hydroxide solution (32% NaOH). Subsequently, the pH is lowered to 1.8 using hydrochloric acid (15% HCl) and at this pH 30 ml of $TiCl_4$ solution (400 g $TiCl_4$/l) are added. The pH during this addition is held constant using aqueous sodium hydroxide solution (32% NaOH). The pH is subsequently raised to 7.5 using aqueous sodium hydroxide solution (32% NaOH) and at this pH a solution of 252 g of sodium silicate (27% $SiO_2$) in 252 g of deionized water is added. During this addition, the pH is kept constant using hydrochloric acid (15% HCl).

Subsequently, the pH is lowered to 2.0 using hydrochloric acid (15% HCl) and at this pH a solution of 3 g of $SnCl_4 \times 5H_2O$ and 10 ml of hydrochloric acid (37% HCl) in 90 ml of deionized water is metered in. During this addition the pH is kept constant using aqueous sodium hydroxide solution (32% NaOH). The pH is subsequently lowered to 1.8 using hydrochloric acid (15% HCl) and at this pH 655 ml of $TiCl_4$ solution (400 g/l) are metered in. During this addition the pH is kept constant using aqueous sodium hydroxide solution (32% NaOH). Following the addition of the $TiCl_4$ solution the mixture is stirred for 15 minutes and the product is filtered off, washed with deionized water, dried at about 110° C. and calcined at 850° C. for 45 minutes. The interference pigment obtained has an intense reddish violet interference colour.

Example 2

100 g of mica (PSD 10–60 μm) in 2 l of deionized water are heated to 80° C. At this temperature, 430 g of iron(III) chloride solution (14.25% Fe) are metered in with vigorous stirring. In the course of this addition, the pH is held constant at 4.0 using aqueous sodium hydroxide solution (32% NaOH). The pH is subsequently raised to 7.5 using aqueous sodium hydroxide solution (32% NaOH) and at this pH a solution of 252 g of sodium silicate (27% $SiO_2$) in 252 g of deionized water is added. During this addition, the pH is kept constant using hydrochloric acid (15% HCl).

Subsequently, the pH is lowered to 2.0 using hydrochloric acid (15% HCl), and a solution of 3 g of $SnCl_4 \times 5H_2O$ and 10 ml of hydrochloric acid (37% HCl) in 90 ml of deionized water is metered in. During this addition the pH is kept constant using aqueous sodium hydroxide solution (32% NaOH). The pH is subsequently lowered to 1.8 using hydrochloric acid (15% HCl), and 476 ml of $TiCl_4$ solution (400 g/l) are metered in. During this addition the pH is kept constant using aqueous sodium hydroxide solution (32% NaOH). Following the addition of the $TiCl_4$ solution the mixture is stirred for 15 minutes and the product is filtered off, washed with deionized water, dried at 110° C. and calcined at 850° C. for 30 minutes. The interference pigment obtained has an intense red interference colour.

Example 3

100 g of muscovite mica (particle size 10–60 μm) in 2 l of deionized water are heated to 80° C. Then, with vigorous stirring, a solution of 3 g of $SnCl_4 \times 5H_2O$ and 10 ml of hydrochloric acid (37% HCl) in 90 ml deionized water is added at a pH of 2.0. During this addition the pH is kept constant using aqueous sodium hydroxide solution (32% NaOH). Subsequently, at a pH of 1.8, 155 ml of $TiCl_4$ solution (400 g $TiCl_4$/l) are added. During this addition the pH is kept constant using aqueous sodium hydroxide solution (32% NaOH). The pH is subsequently raised to 2.6 using aqueous sodium hydroxide solution and at this pH 100 ml of a solution of 25 ml of $TiCl_4$ solution (400 g $TiCl_4$/l), 48 g of $FeCl_3$ solution (14.25% Fe) and 4.8 g of $AlCl_3 \times 6H_2O$ in deionized water are added. During this addition the pH is kept constant using aqueous sodium hydroxide solution (32% NaOH).

The pH is subsequently raised to 7.5 using aqueous sodium hydroxide solution (32% NaOH) and at this pH a solution of 271 g of sodium silicate (27% $SiO_2$) in 271 g of deionized water is metered in. The pH is kept constant using hydrochloric acid (10% HCl). The pH is subsequently lowered to 2.0 using hydrochloric acid (10% HCl), and a solution of 3 g of $SnCl_4 \times 5H_2O$ and 10 ml of hydrochloric acid (37% HCl) in 90 ml of deionized water is metered in. During this addition the pH is kept constant using aqueous sodium hydroxide solution (50% NaOH). Subsequently, at a pH of 1.8, 45 ml of $TiCl_4$ solution (400 g $TiCl_4$/l) are added, the pH again being kept constant using aqueous sodium hydroxide solution (32% NaOH). Thereafter the pH is raised to 2.6 using aqueous sodium hydroxide solution (32% NaOH) and at this pH 230 ml of a solution of 129 ml of $TiCl_4$ solution (400 g $TiCl_4$/l), 206 g of $FeCl_3$ solution (14.25% Fe) and 10.2 g $AlCl_3 \times 6H_2O$ in 157 ml of deionized water are metered in. During this addition the pH is kept constant using aqueous sodium hydroxide solution (32% NaOH). Finally the pigment is filtered off with suction, washed with deionized water, dried at 110° C. and calcined at 850° C. for 30 minutes. The result is an interference pigment with an intense reddish violet colour which flips through orange to a strong yellowish green.

Example 4

The dried pigment from Example 2 is calcined at 850° C. for 30 minutes in a forming-gas atmosphere ($N_2/H_2$; 85/15). The pigment prepared in this way exhibits an intense bronze effect and a strong lustre.

Example 5

100 g of muscovite mica (particle size 10–60 μm) in 2 l of deionized water are heated to 80° C. Then, with vigorous stirring, a solution of 3 g of $SnCl_4 \times 5H_2O$ and 10 ml of hydrochloric acid (37% HCl) in 90 ml deionized water is added at a metering rate of 4 ml/min at a pH of 2.0. During this addition the pH is kept constant using aqueous sodium hydroxide solution (32% NaOH). Subsequently, at a pH of 1.8, 155 ml of $TiCl_4$ solution (400 g $TiCl_4$/l) are added at a metering rate of 2 ml/min. During this addition the pH is kept constant using aqueous sodium hydroxide solution (32% NaOH). The pH is subsequently raised to 2.6 using aqueous sodium hydroxide solution and at this pH 100 ml of a solution of 25 ml of $TiCl_4$ solution (400 g $TiCl_4$/l), 48 g of $FeCl_3$ solution (14.25% Fe) and 4.8 g of $AlCl_3 \times 6H_2O$ in deionized water are added. During this addition the pH is kept constant using aqueous sodium hydroxide solution (32% NaOH).

The pH is subsequently raised to 7.5 using aqueous sodium hydroxide solution (32% NaOH) and at this pH a solution of 297 g of sodium silicate (27% $SiO_2$) in 297 g of deionized water is metered in at a rate of 2 ml/min. The pH is kept constant using hydrochloric acid (10% HCl). The pH is subsequently lowered to 2.0 using hydrochloric acid (10% HCl), and a solution of 3 g of $SnCl_4 \times 5H_2O$ and 10 ml of hydrochloric acid (37% HCl) in 90 ml of deionized water is metered in at a rate of 4 ml/min. During this addition the pH is kept constant using aqueous sodium hydroxide solution (32% NaOH). Subsequently, at a pH of 1.8, 250.5 ml of $TiCl_4$ solution (400 g $TiCl_4$/l) are added at a rate of 2 ml/min, the pH again being kept constant using aqueous sodium hydroxide solution (32% NaOH).

Subsequently the pigment is filtered off with suction, washed with deionized water and dried at 110° C. Following this stage the pigment obtained has a reddish violet colour which flips to yellowish green.

Finally, the pigment is calcined at 850° C. for 30 minutes. The result is an interference pigment with a yellowish red lustre whose colour flips to a yellowish green.

Example 6

The metal oxide layers are precipitated as in Example 5. In addition, at a pH of 2.6, 130 ml of a mixture of 129 ml of $TiCl_4$ solution (400 g $TiCl_4$/l) 147 ml of $FeCl_3$ solution (14.08% Fe), 10.2 g of $AlCl_3 \times 6H_2O$ and 157 ml of deionized water are added at a metering rate of 1 ml/min. During this addition the pH is kept constant using aqueous sodium hydroxide solution (32% NaOH).

The pigment is worked up as in Examples 1–5.

The dried pigment exhibits an intense reddish violet colour of high lustre, which flips to orange. After calcination, the pigment has a yellowish red lustre, with the colour flipping to a strongly lustrous yellow.

Example 7

The dried product from Example 4 is calcined at 850° C. for 30 minutes in a forming-gas atmosphere ($N_2/H_2$; 85/15). The pigment prepared in this way exhibits a red bronze effect and strong lustre and also heightened opacity. On flipping, the colour changes to a strong yellowish green.

Example 8

The dried product from Example 5 is calcined at 850° C. for 30 minutes in a forming-gas atmosphere ($N_2/H_2$; 85/15). The pigment prepared in this way exhibits a deep red bronze effect and strong lustre and also heightened opacity. On flipping, the colour changes to a strong golden yellow.

What is claimed is:

1. An interference pigment comprising a multiply coated, platelet-shaped substrate (S) having at least one layer sequence comprising
   (A) a coating having a refractive index n>2.0,
   (B) a colourless coating having a refractive index n>1.8, and
   (C) a nonabsorbing coating of high refractive index.

2. The interference pigment according to claim 1, wherein between the substrate (S) and the layer (A), the layer (A) and (B), and/or the layer (B) and (C) there is a further colored or colorless metal oxide layer (S1), (A1), (B1) and/or (C1).

3. The interference pigment according to claim 1, wherein the platelet-shaped substrate is natural or synthetic mica, glass, $Al_2O_3$, $SiO_2$ or $TiO_2$ flakes, or a platelet-shaped material coated with at least one metal oxide.

4. The interference pigment according to claim 1, wherein the layers (A), (B) and (C) consist essentially of metal oxides.

5. The interference pigment according to claim 1, wherein the layer (A) consists essentially of titanium dioxide, iron oxide, bismuth oxychloride, zirconium oxide, tin oxide, zinc oxide, titanium suboxides, iron titanates, iron oxide hydrates, chromium oxide, bismuth vanadate, cobalt aluminate or a mixture thereof.

6. The interference pigment according to claim 1, wherein the layer (B) consists essentially of silicon dioxide, aluminum oxide, magnesium fluoride or a mixture thereof.

7. The interference pigment according to claim 1, wherein the layer (C) consist essentially of titanium dioxide, bismuth oxychloride, zirconium oxide, tin oxide, zinc oxide or a mixture thereof.

8. The interference pigment according to claim 1, having the layer sequence (A)–(C) up to four times.

9. The interference pigment according to claim 8, containing only one layer sequence (A)–(C).

10. A process for preparing an interference pigment according to claim 1, comprising applying the metal oxides wet-chemically to the platelet-shaped substrate by hydrolytic decomposition of metal salts in an aqueous medium.

11. A paint, lacquer, printing ink, plastic, ceramic material, glass or cosmetic formulation, comprising an interference pigment according to claim 1.

12. The interference pigment according to claim 1, further comprising (D) an external protective layer.

13. An interference pigment comprising a multiply coated, platelet-shaped substrate having at least one layer sequence comprising (A) a coating having a refractive index n>2.0, selected from the group consisting of iron oxide, bismuth oxychloride, zirconium oxide, bismuth vanadate, cobalt aluminate or a mixture thereof, (B) a colourless coating having a refractive index n>1.8, selected from the group consisting of titanium dioxide, tin oxide, zinc oxide or a mixture thereof, (C) a nonabsorbing coating of high refractive index, and, (D) an external protective layer.

* * * * *